United States Patent
Gencheff (10) Patent No.: US 9,931,135 B2
(45) Date of Patent: Apr. 3, 2018

(54) METHOD OF PENETRATING AN INTRAVASCULAR OCCLUSION

(71) Applicant: Frontier Medical Devices, Inc., Marquette, MI (US)

(72) Inventor: Nelson E. Gencheff, Marquette, MI (US)

(*) Notice: Subject to any disclaimer, the term of this patent is extended or adjusted under 35 U.S.C. 154(b) by 219 days.

(21) Appl. No.: 14/531,691

(22) Filed: Nov. 3, 2014

(65) Prior Publication Data

US 2015/0057694 A1 Feb. 26, 2015

Related U.S. Application Data

(63) Continuation-in-part of application No. 14/185,782, filed on Feb. 20, 2014, now abandoned.

(60) Provisional application No. 61/766,796, filed on Feb. 20, 2013.

(51) Int. Cl.
*A61B 17/32* (2006.01)
*A61B 17/3207* (2006.01)
*A61B 17/22* (2006.01)
*A61B 17/34* (2006.01)

(52) U.S. Cl.
CPC .... *A61B 17/3207* (2013.01); *A61B 17/32002* (2013.01); *A61B 17/320016* (2013.01); *A61B 17/320758* (2013.01); *A61B 17/3403* (2013.01); *A61B 2017/22038* (2013.01); *A61B 2017/22044* (2013.01); *A61B 2017/22048* (2013.01); *A61B 2017/22067* (2013.01); *A61B 2017/22069* (2013.01); *A61B 2017/22094* (2013.01); *A61B 2017/346* (2013.01); *A61B 2017/3486* (2013.01)

(58) Field of Classification Search
CPC ........ A61B 17/3207; A61B 17/320758; A61B 17/320016; A61B 17/32002; A61B 17/3403; A61B 2017/22038; A61B 2017/22044; A61B 2017/22048; A61B 2017/22067; A61B 2017/22069; A61B 2017/22094; A61B 2017/320032; A61B 2017/320052; A61B 2017/320056; A61B 2017/320072; A61B 2017/346; A61B 2017/3486

See application file for complete search history.

(56) References Cited

U.S. PATENT DOCUMENTS

| | | | | |
|---|---|---|---|---|
| 5,423,846 | A * | 6/1995 | Fischell | A61B 17/3207 606/172 |
| 5,527,298 | A * | 6/1996 | Vance | A61M 29/00 600/585 |
| 8,109,953 | B1 * | 2/2012 | King, III | A61B 17/22 606/159 |

(Continued)

*Primary Examiner* — Robert Lynch (57) ABSTRACT

A method of penetrating an intravascular occlusion including the steps of: obtaining an apparatus with a sleeve assembly defining an elongate passageway having a lengthwise axis, a stabilizing assembly, and a blade assembly; directing the sleeve assembly into an operative position within a vessel passage wherein an outlet from the elongate passageway is adjacent an occlusion within the vessel passage; through the stabilizing assembly, stabilizing the sleeve assembly in the operative position; and with the sleeve assembly stabilized in its operative position advancing the blade assembly in a first lengthwise direction relative to the sleeve assembly to penetrate the occlusion.

26 Claims, 5 Drawing Sheets

(56) References Cited

U.S. PATENT DOCUMENTS

| | | | |
|---|---|---|---|
| 2006/0015126 A1* | 1/2006 | Sher | A61B 17/320758 606/159 |
| 2006/0293612 A1* | 12/2006 | Jenson | A61B 17/3207 600/585 |
| 2007/0255270 A1* | 11/2007 | Carney | A61B 17/320758 606/35 |
| 2010/0049225 A1* | 2/2010 | To | A61B 17/320758 606/159 |
| 2011/0160755 A1* | 6/2011 | McGhie | A61B 17/3207 606/159 |
| 2012/0203163 A1* | 8/2012 | Thomas | A61B 17/320758 604/22 |

* cited by examiner

METHOD OF PENETRATING AN INTRAVASCULAR OCCLUSION

CROSS-REFERENCE TO RELATED APPLICATIONS

This application is a continuation-in-part of U.S. patent application Ser. No. 14/185,782, filed Feb. 20, 2014

BACKGROUND OF THE INVENTION

Field of the Invention

This invention relates to intravascular procedures and, more particularly, to a method of penetrating an intravascular occlusion to facilitate passage of a device therethrough.

Background Art

In the performance of many intravascular procedures, chronic total or subtotal occlusions may be encountered within arterial passages. Current percutaneous revascularization methods frequently lead to complications, among which are vessel perforation, subintimal space entry, and extensive vascular dissection planes. These complications commonly arise due to the inability to penetrate the proximal occlusive calcified fibrous cap which has a potentially complex surface geometry. Failed fibrous cap penetration may lead to misalignment of guide wires or devices needed to revascularize a target vessel. Misalignment and/or deflection of wires or devices further fosters dissection planes and vessel perforation which may necessitate termination of a revascularization procedure. These occurrences typically result in failure to revascularize the target vessel and may lead to significant patient morbidity or mortality, compartment syndrome, bleeding, critical limb ischemia, limb loss, etc.

Available peripheral vascular tools have not addressed the vascular fibrous cap domain in either a safe or cost-effective fashion. A practical device dedicated to penetration of intravascular occlusions, including at the proximal fibrous cap, and intralumenal wire migration should be simple in design, user friendly, and affordable with regard to both institutional budgets and industry production.

SUMMARY OF THE INVENTION

In one form, the invention is directed to a method of penetrating an intravascular occlusion. The method includes the steps of: obtaining an apparatus with a sleeve assembly defining an elongate passageway with a lengthwise axis, a stabilizing assembly, and a blade assembly; directing the sleeve assembly into an operative position within a vessel passage wherein an outlet from the elongate passageway is adjacent an occlusion within the vessel passage; through the stabilizing assembly, stabilizing the sleeve assembly in the operative position; and with the sleeve assembly stabilized in its operative position advancing the blade assembly in a first lengthwise direction relative to the sleeve assembly to penetrate the occlusion.

In one form, the stabilizing assembly has an elongate probe with a penetrating tip. The step of stabilizing the sleeve assembly involves advancing the elongate probe in the first lengthwise direction to cause the penetrating tip to penetrate the occlusion.

In one form, the stabilizing assembly is changeable between first and second states. The stabilizing assembly is configured to be extended radially outwardly from the sleeve assembly as the stabilizing assembly is changed from its first state into its second state to thereby limit radial skewing of the sleeve assembly within the vessel passage.

In one form, the stabilizing assembly has an inflatable bladder. The step of stabilizing the sleeve assembly involves inflating the bladder to thereby change the stabilizing assembly from its first state into its second state.

In one form, the blade assembly has a plurality of blades that taper to a tip. The step of advancing the blade assembly involves advancing the blade assembly tip forward in the first lengthwise direction into the occlusion.

In one form, the step of advancing the blade assembly involves guiding the blade assembly against and relative to the elongate probe.

In one form, the penetrating tip has a granular component thereon to facilitate penetration of the occlusion.

In one form, the method further includes the step of directing a guide wire into the vessel passage toward the occlusion. The step of directing the sleeve assembly into its operative position involves guiding the sleeve assembly along the guide wire in the first lengthwise direction.

In one form, the stabilizing assembly has an elongate probe with a penetrating tip. The step of stabilizing the sleeve assembly involves advancing the elongate probe in the first lengthwise direction to cause the penetrating tip to penetrate the occlusion. The method further includes the step of removing the guide wire from the passageway before directing the elongate probe into the passageway.

In one form, the method further includes the step of advancing a guide wire through the occlusion after the blade assembly has penetrated fully through the occlusion and thereafter removing the blade assembly from the passageway.

In one form, the stabilizing assembly further includes a guide wire. The step of stabilizing the sleeve assembly involves directing the guide wire in the first longitudinal direction into the occlusion after which the bladder is changed from its first state into its second state.

In one form, the method further includes the steps of removing the guide wire, directing an elongate probe with a penetrating tip into the passageway in the first longitudinal direction so that the penetrating tip penetrates the occlusion, and thereafter advancing the blade assembly in the first longitudinal direction against and relative to the elongate probe and into the occlusion.

In one form, the method further includes the steps of removing the elongate probe and blade assembly after the occlusion has been fully penetrated and thereafter directing a guide wire into the passageway in the first longitudinal direction and to and through the occlusion with the elongate probe removed.

In one form, the method further includes the step of guiding a device through the passageway and over and against the guide wire through the occlusion to allow performance of a procedure by the device within the vessel passage past the occlusion.

In one form, the method further includes the step of rotating at least one of the penetrating tip and blade assembly around an axis to penetrate the occlusion.

In one form, the step of advancing the blade assembly involves advancing the blade assembly in a curved path within the vessel passage and thereby causing the blades to bend to conform to the curved path.

In one form, the sleeve assembly has a tapered annular surface that reduces in diameter in the first lengthwise direction. The step of advancing the blade assembly involves advancing the blade assembly guidingly against the tapered annular surface.

In one form, the invention is directed to the apparatus for penetrating an intravascular occlusion as recited above.

In one form, the stabilizing assembly is changeable between first and second states. The stabilizing assembly is configured to be extended radially outwardly from the sleeve assembly as the stabilizing assembly is changed from its first state into its second state to thereby limit radial skewing of the sleeve assembly within the vessel passage.

In one form, the stabilizing assembly has one of: a) an elongate probe with a stabilizing tip; and b) a guide wire.

DETAILED DESCRIPTION OF THE PREFERRED EMBODIMENT

Figure 1:
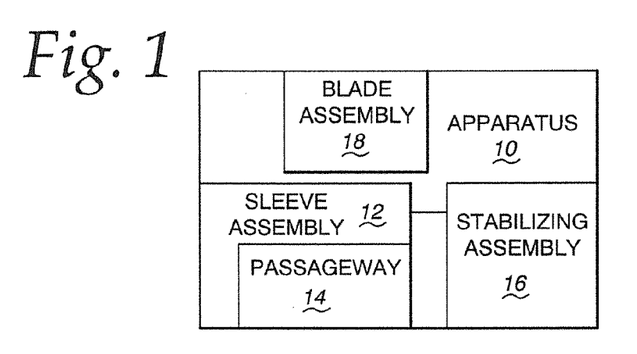
FIG. 1 is a schematic representation of an apparatus, according to the invention, for penetrating an intravascular occlusion.

An apparatus, according to the present invention, usable to penetrate an intravascular occlusion, is shown in schematic form at 10 in FIG. 1. The apparatus 10 is made up of a sleeve assembly 12 that defines an elongate passageway 14 with a lengthwise axis, a stabilizing assembly 16, and a blade assembly 18. The schematic showing of these components is intended to encompass the specific embodiments hereinbelow as well as other variations of the components therein and their interaction.

Figure 2:
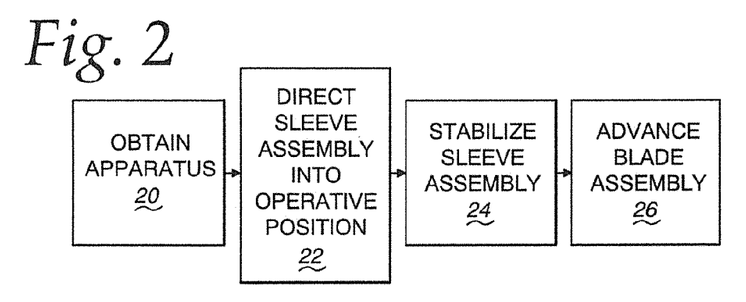
FIG. 2 is a flow diagram representation of a method of penetrating an intravascular occlusion, according to the present invention, using the apparatus in FIG. 1.

With the basic apparatus, a method of penetrating an intravascular occlusion, according to the present invention, can be carried out as shown in flow diagram form in FIG. 2.

As shown at block 20, an apparatus as shown at 10 in FIG. 1 is obtained.

As shown at block 22, the sleeve assembly 12 is directed into an operative position within a vessel passage wherein an outlet from the elongate passageway 14 is adjacent an occlusion within a vessel passage.

As shown at block 24, the sleeve assembly 12 is stabilized in its operative position through the stabilizing assembly 16.

As shown at block 26, with the sleeve assembly 12 stabilized in its operative position, the blade assembly 18 is advanced in a first lengthwise direction relative to the sleeve assembly 12 to penetrate the occlusion.

Specific embodiments of the above apparatus and method will now be described with respective FIGS. 3-9, in relationship to a vessel passage 28 at which there is an occlusion 30.

Figure 3:
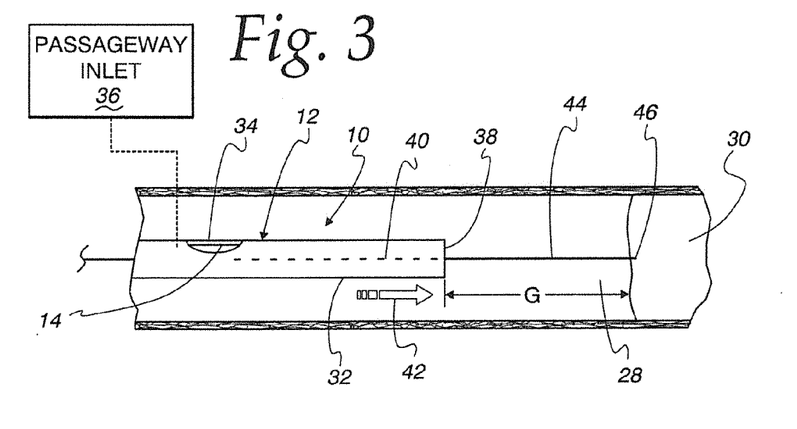
FIGS. 3-5 are fragmentary elevation views of a portion of the apparatus in FIG. 1 within a representative vessel passage and showing a sequence of initial steps carried out to penetrate a vascular occlusion.

The sleeve assembly 12 on the apparatus 10 consists of a tubular portion 32 with a tubular wall 34 that, by itself or in conjunction with one or more other components, bounds the passageway 14.

The passageway 14 has a proximal inlet 36 and an outlet 38. The sleeve assembly 12 and passageway 14 have a central, lengthwise axis 40 between the inlet 36 and outlet 38.

To initiate the inventive method, the sleeve assembly 12 is directed into the vessel passage 28 in a first lengthwise direction, as indicated by the arrow 42 into an operative position. Preferably this is done by first directing a guide wire 44 into the vessel passage 28 so that the free end 46 of the guide wire 44 is pressed into the material defining the occlusion 30 so that the material defining the occlusion 30 closely surrounds and thereby stabilizes the free end 46 of the guide wire 44. The use of a guide wire is not a requirement.

The tubular portion 32 is advanced until the outlet 38 is adjacent to the occlusion 30. While the tubular portion 32 could be advanced to against the occlusion 30, the method is more preferably carried out with a gap G between the outlet 38 and occlusion 30. In the FIG. 3 position, the guide wire 44 makes up part of the stabilizing assembly 16.

Figure 4:
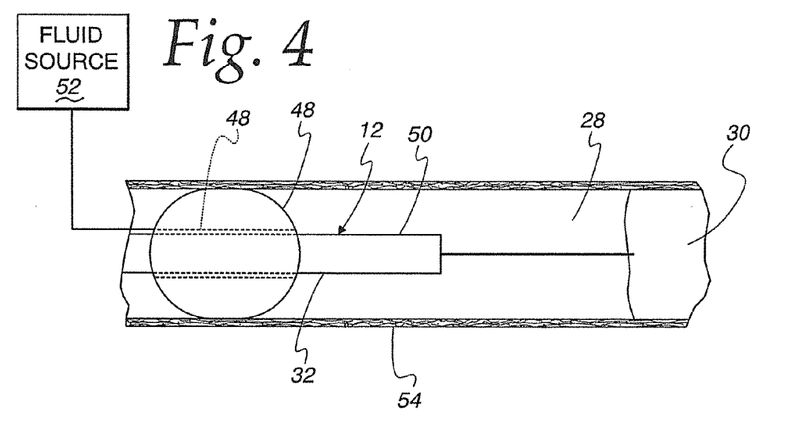

The stabilizing assembly 16 further includes an inflatable bladder 48 that is changeable between first and second states. In the first state, the bladder 48 is collapsed towards an outside surface 50 on the tubular portion 32 adequately that it will not significantly inhibit movement of the tubular portion 32 through the vessel passage 28 upstream of the occlusion 30. Through a pressurized fluid source 52 (FIG. 2), the bladder 48 can be inflated to be placed in a second state wherein it produces a doughnut shape around the tubular portion 32, thereby centering the tubular portion 32 within the vessel passage 28. This stabilizes the sleeve assembly 12 primarily by preventing radial skewing. Further, the enlarged bladder 48 produces a resilient biasing force between the wall 54 of the vessel passage 28 and the sleeve assembly 12, thereby to inhibit axial movement of the sleeve assembly 12 relative to the vessel wall 54.

While a bladder configuration is one preferred form of the stabilizing assembly 16, it is contemplated that, within the generic showing in FIG. 1, the stabilizing assembly 16 may take myriad different constructions, generally designed to be extended radially outwardly from the sleeve assembly 12 as the stabilizing assembly 16 is changed from its first state into its second state to thereby limit principally radial skewing of the sleeve assembly 12 within the vessel passage 28.

Figure 5:
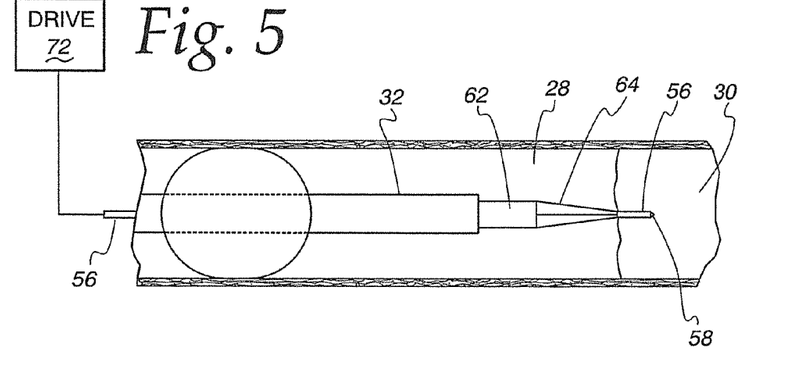

In this embodiment, the stabilizing assembly 16 further includes an elongate probe 56 with a penetrating tip 58 shown in FIGS. 5-8. Preferably, the guide wire 44 is withdrawn beforehand. Alternatively, the probe 56 could have a passageway to accommodate the guide wire 44. The sleeve assembly 12 is stabilized by advancing the elongate probe 56 in the first lengthwise direction to cause the penetrating tip 58 to penetrate the occlusion 30, as shown in FIG. 5.

Figure 6:
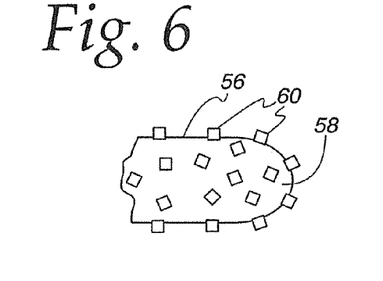
FIG. 6 is an enlarged, fragmentary, elevation view of a tip on one of the components making up a stabilizing assembly on the inventive apparatus.

The penetrating tip 58 may have a granular component thereon to facilitate penetration of the occlusion 30. As one example, the penetrating tip 58 may be coated with diamond granules 60, as shown in FIG. 6, to create an abrasive surface.

The blade assembly 18 has an axis and consists of a shaft 62 with a plurality of blades 64 at its distal end. The blade assembly axis aligns with the length of the vessel passage 28. The proximal end of the shaft 62 is connected to a drive 66 that may be simply a handle that is graspable by a user or an automated device, as described hereinafter.

The blade assembly 18 has an elongate passageway 68 that extends fully through the length thereof, including through the region at which the blades 64 are formed.

Figure 10:
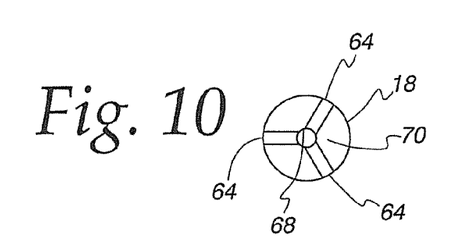
FIG. 10 is a front elevation view of a blade assembly on the inventive apparatus.

As shown in FIG. 10, there are three blades 64 projecting from a hub 70 that surrounds the passageway 68. The hub 70 may be a fixed part of the shaft 62. Alternatively, the hub 70 and blades 64 may make up a separate cutting head. Each of the blades 64 has a generally flat body with a plane that passes through the passageway 68 and is aligned with the length of the passage. The blades 64 are spaced angularly equidistantly from each other around the axis of the hub 70. The bodies of the blades 64 each has a "fin" shape that projects radially. The blades 64 may be made from stainless steel.

Figure 7:
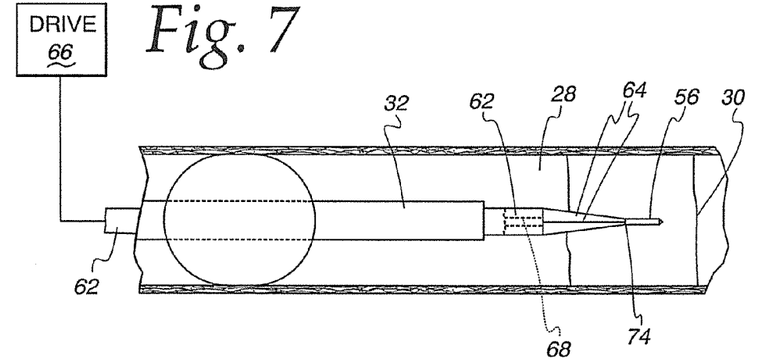
FIGS. 7-9 correspond to FIGS. 3-5 and show an additional sequence of steps carried out to complete the penetration of an intravascular occlusion.

The passageway 68 has a large enough diameter to accommodate the elongate probe 56, which is slidable guidingly therethrough. After the elongate probe 56 penetrates the occlusion 30 to a first depth, it may be advanced forwardly relative to the blade assembly 18 as shown in FIG. 7. The elongate probe 56 may be controlled through an appropriate drive 72 that may be the same in nature as the drive 66.

Once in the FIG. 7 position, the tip 74 of the blade assembly 18 can be advanced forwardly in the first lengthwise direction further into the occlusion 30 to eventually produce a bore 76 approximately equal to the diameter of the shaft 62. As this occurs, the blade assembly 18 is stably supported for guided relative movement in the first lengthwise direction by both the tubular portion 32 and the elongate probe 56.

Figure 8:
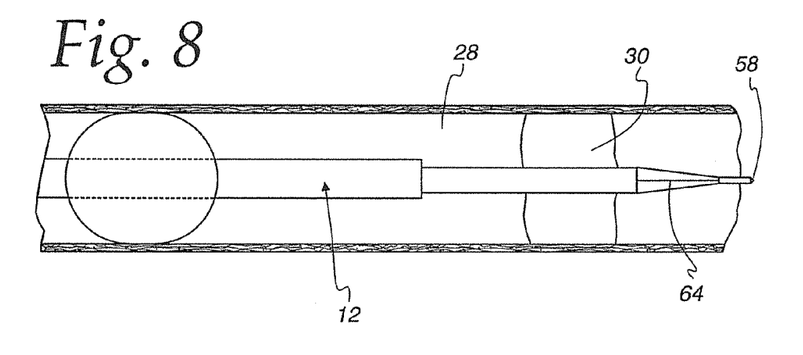

FIG. 8 shows the blades 64 and penetrating tip 58 extended fully through the occlusion 30 to form an enlarged bore diameter. Thereafter, the elongate probe 56 can be retracted and the guide wire 44 reinserted, preferably with the blade assembly 18 still in place. Thereafter, the blade assembly 18 can be withdrawn, leaving the guide wire 44 extended fully through the bore 76 formed in the occlusion 30.

Figure 9:
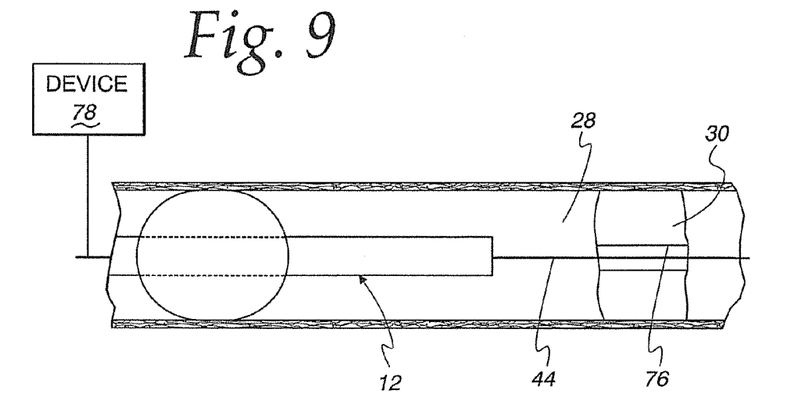

Thereafter, as shown in FIG. 9, an appropriate device 78 can be directed into the vessel passage 28 through the sleeve assembly 12, guided by the guide wire 44. The device 78 can be any conventional device used to perform intravascular procedures. The bore 76 is dimensioned to accommodate such conventional devices 78 such that portions of the device 78 to be used downstream of the occlusion 30 can be extended past the occlusion 30.

As noted above, the drives 66, 72 can be operated to rotate and/or otherwise manipulate the blade assembly 18 and/or elongate probe 56 to facilitate penetration of the occlusion 30.

It should be understood that different combinations of steps utilizing the components shown in FIGS. 3-10 might be utilized. The described procedure is just exemplary in nature. For example, the elongate probe 56 need not be utilized to carry out the process under certain circumstances.

Figures 11, 12, 13:
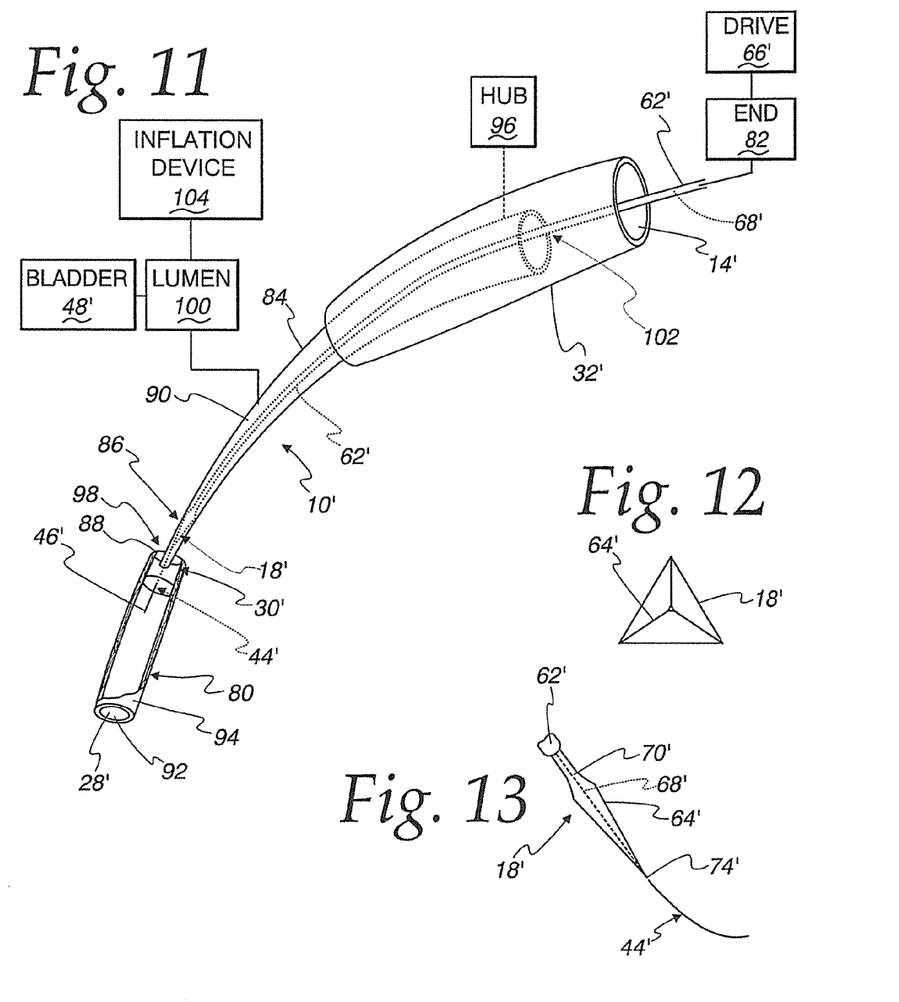
FIG. 11 is a perspective view of another form of apparatus, according to the present invention, in relationship to a vessel with an occlusion therein.
FIG. 12 is an end elevation view of a blade assembly on the apparatus in FIG. 11.
FIG. 13 is a fragmentary, elevation view of the blade assembly in FIGS. 11 and 12 and with a guide wire extending therethrough.

A modified form of the inventive apparatus is shown at 10' in FIGS. 11-13, wherein parts corresponding to those in FIGS. 1 and 3-10 are identified with the same reference numerals with the addition of a "'" designation.

A blade assembly 18' has a plurality of blades 64' arranged on a hub 70' in substantially the same manner as the aforementioned blades 64 are arranged on the hub 70.

In this embodiment, the blade assembly 18' has a passageway 68' to accommodate a guide wire 44'. The passageway 68' is preferably of large enough diameter to accommodate a guide wire 44' that may be on the order of 0.018 mm. As in the prior embodiment, the blades 64' converge to a tip 74' having a diameter of approximately 0.019 mm.

The lengths and shapes of the blades 64' are selected to allow passage across a contralateral vessel 80 bent at an angle of 25°-30°. Accordingly, the blades 64' must be adequately flexible to conform to this bend. The use of the guide wire 44' facilitates conforming of the blade assembly 18' to this geometry. However, use of the guide wire 44' is not a requirement.

The blades 64' are attached at the distal end of a drive shaft 62' that may be constructed of flexible steel. The passageway 68' extends through the shaft 62' and is large enough to accommodate a guide wire diameter generally in the range from 0.014 to 0.019 mm. The steel construction of the drive shaft 62' allows the blades 64' to be advanced with a sizable force applied by the user without excessive bending or buckling.

The length of the shaft 62' preferably exceeds the overall length of the remainder of the apparatus 10', including a tubular portion 32' and any additional component(s) that in conjunction therewith define a passageway 14'. The proximal end 82 of the shaft 62' may be manually engaged to be manipulated or engaged by a drive 66'.

In this embodiment, a tubular blade magazine 84 is provided within the tubular portion 32'. The blade magazine 84 may be constructed of a non-metal, flexible material extruded in such a manner that a distal end 86 thereof is tapered but large enough to allow for passage of the blades 64' upon the hub 70'. The tapering design provides support to the blade elements 64' to facilitate controlled penetration and successful crossing of the exemplary, depicted, proximate, occlusive, calcified, fibrous cap 88 at an end of the occlusion 30'.

The external surface 90 of the blade magazine 84 may be coated with a lubricious material to control frictional resistance encountered within the tubular portion 32' and also with the inside surface 92 of the vessel 94 bounding the passage 28' into which the apparatus 10' is directed.

The proximal end of the blade magazine 84 terminates at a hub 96 that is compatible with standard sized stopcocks or other connecting elements needed for a procedure.

This design also facilitates passage of the blade magazine 84 into that portion 98 of the vessel at 94 incised by the blades 64'.

Upon successful penetration of the proximal fibrous cap 88, the user may direct the guide wire 44', or a different guide wire, to access the vessel 94 downstream of the occlusion 30'.

The blade magazine 84 may incorporate an inflatable bladder 48' or other structure corresponding to that in the stabilizing assembly 16, previously described. In the event of the use of the bladder 48', the bladder 48' is preferably attached to the distal one-third of the blade magazine 84. The bladder 48' may communicate with an extrusion lumen 100 that terminates at the proximal end 102 of the magazine 84, to allow a user to fill the bladder 48' through an appropriate inflation device 104. As with the earlier described embodiment, the bladder 48' facilitates centering of the blade magazine 84 within the vessel 94 and promotes centering of the blade elements 64' at the fibrous cap 88. The bladder 48' further stabilizes the blade magazine 84 and the blade elements 64' during operation.

A procedure is carried out with the apparatus 10' in substantially the same manner as carried out with the apparatus 10, as previously described. One exemplary process will now be described.

It is desirable to penetrate the fibrous cap 88 in proximity to the center of the vessel 94. The blade magazine 84 acts as a guide to promote blade positioning. The blade magazine 84 is preferably brought into proximity with the fibrous cap 88 before the blades 64 are exposed/deployed. The tapered blade configuration also acts to optimize central positioning of the blades 64'.

The guide wire 44' has a sharp tip/free end 46' to foster cap penetration and successful blade migration through the cap 88 and vascular occlusive segment 30'. After successful penetration of the proximal fibrous cap 88 and wire entry into the true unobstructed vascular vessel passage 28', the same drive shaft wire 44' may be used or replaced with a smaller diameter floppy wire, having a diameter on the order of 0.014-0.018 mm, to allow completion of the procedure preparatory to using the device 78.

Figure 14:
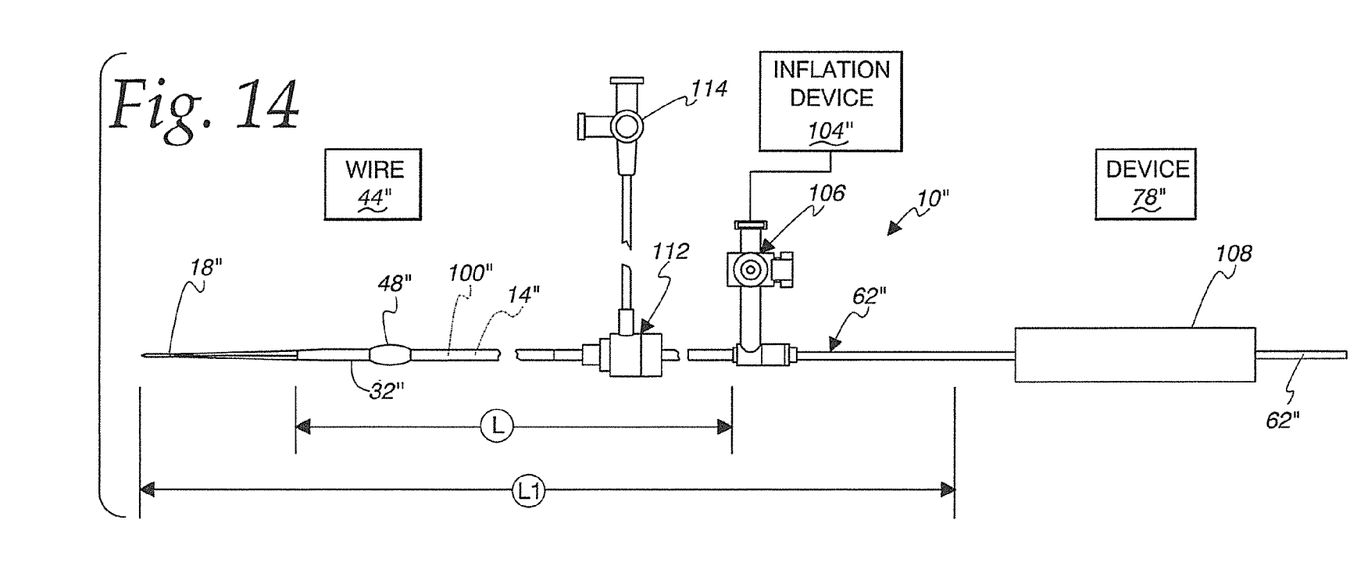
FIG. 14 is a side elevation view of a further modified form of apparatus, according to the invention.
Figure 15:
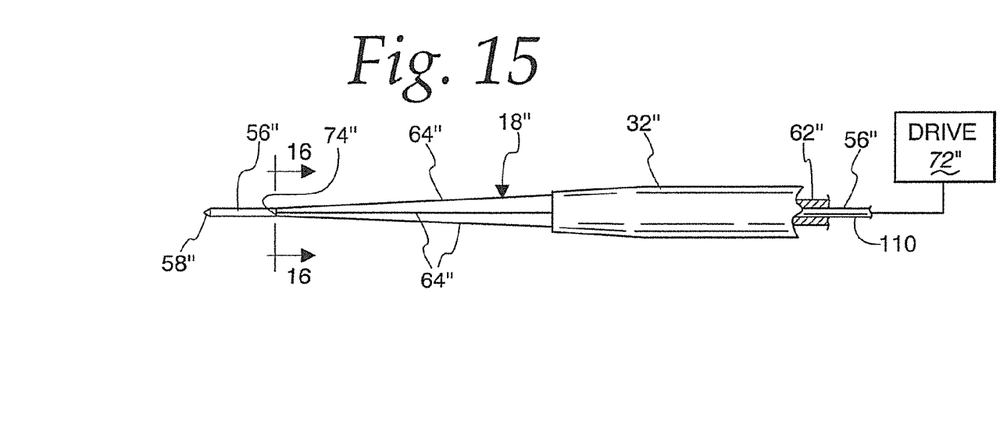
FIG. 15 is an enlarged view of the region within the circle A in FIG. 14.
Figure 16:
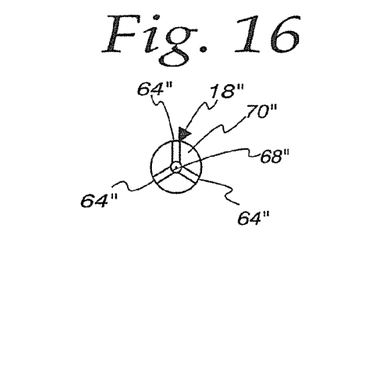
FIG. 16 is a cross-sectional view of the blade assembly taken along line 16-16 of FIG. 15.

In FIGS. 14-16, a further modified form of apparatus, according to the present invention, is shown at 10". The blade assembly 18" has three blades 64" made from 440 stainless steel, or another material of similar Rockwell hardness. The blades are arranged, three in number, around the hub 70". The blades 64" converge to a tip 74".

The blade assembly 18" further consists of a drive shaft 62". The shaft 62" and hub 70" have a passageway 68" formed therethrough. The shaft 62" is preferably a semi-rigid metallic component. The shaft 62" and blades 64" are contained in an extruded tubular portion 32", which is tapered at its distal end and coated with a lubricious material, interiorly and exteriorly. The tubular portion 32" acts as the aforementioned blade magazine 84 and facilitates central intravascular positioning of the blades 64" while also providing support therefor during use.

The tubular portion 32" has an inflatable bladder 48" thereon that functions as the aforementioned bladders 48, 48' on their respective apparatus. An extrusion lumen 100" terminates at an inflation hub 106 which is compatible with standard inflation devices 104".

An external drive shaft handle 108 is used by an operator to control the blade assembly 18".

In this embodiment, an elongate probe 56" passes through the blade assembly 18" and extends beyond the blade assembly 18", as shown in FIG. 15. The elongate probe 56" may be made from 0.018 inch piercing wire. The penetrating tip 58" tapers and is coated with diamond granules in order to create an abrasive surface. The proximal end 110 of the elongate probe 56" is engaged with a drive 72" through an attachment structure that is compatible with an external motor unit.

The elongate probe 56" and blades 64" can be used in unison to migrate across an occlusion 30, as shown using the other inventive embodiment in FIGS. 3-9.

Prior to activation of the blade assembly 18" and elongate probe 56", the bladder 48" is inflated, in the same manner as described for previous embodiments, to limit the opportunity for wire deflection or subintimal space entry.

Once successful migration through the occlusion has been achieved, the elongate probe 56 may be exchanged for a standard 0.018 inch guide wire 44" or a smaller working wire. Once the wire 44" is introduced to the vessel passage and passed through the penetrated occlusion, the entire apparatus 10" can be removed over the wire 44" and exchanged for other appropriate intravascular devices 78" in order to complete the desired revascularization procedure.

In the event that the elongate probe 56" is unable to score the occlusion, which may have the aforementioned fibrous cap, it may be connected to a pneumatically-powered external drive unit 72" and used as a drill with a hammer-like motion to facilitate micro fracturing of the central fibrous cap. Subsequently, migration of the blades 64" is carried out, to promote intralumenal wire positioning.

The apparatus 10" may be directed through a sheath that is intravascularly situated. Accordingly, the sizing of the apparatus 10" is controlled to be compatible with standard sized working sheaths.

In FIG. 14, a port 112 is shown communicating with the passageway 14" defined by the apparatus 10". A monitoring and injection valve 114 communicates with the port 112.

Representative lengthwise dimensions are shown for the system with the dimension L being a representative 100 cm and the dimension L1 being a representative 130 cm.

The foregoing disclosure of specific embodiments is intended to be illustrative of the broad concepts comprehended by the invention.

The inventive apparatus has the potential to be used safely to penetrate subtotal or total arterial occlusion while being user friendly and affordable. It is also potentially compatible with existing technology. Successful penetration of an occlusion/fibrous cap, and maintenance of intralumenal position during revascularization of ischemic tissue is an important endpoint, which has a direct influence on procedural success, procedural time, and procedural costs.

The invention claimed is:

1. A method of penetrating an intravascular occlusion, the method comprising the steps of:
   obtaining an apparatus comprising a sleeve assembly defining an elongate passageway with a lengthwise axis, a stabilizing assembly, and a blade assembly with a sharp cutting edge;
   directing the sleeve assembly into an operative position within a vessel passage wherein an outlet from the elongate passageway is adjacent an occlusion within the vessel passage;
   through the stabilizing assembly, stabilizing the sleeve assembly in the operative position at spaced axial locations wherein at one of the spaced axial locations a part of the stabilizing assembly is stabilized by the occlusion,
   wherein the stabilizing assembly is changeable between first and second states, another part of the stabilizing assembly configured to be extended radially outwardly from the sleeve assembly as the stabilizing assembly is changed from the first state into the second state,
   wherein the step of stabilizing the sleeve assembly comprises changing the stabilizing assembly from the first state into the second state while maintaining the part of the stabilizing assembly stabilized by the occlusion; and
   with the sleeve assembly stabilized in its operative position advancing the blade assembly in a first lengthwise direction relative to the sleeve assembly to penetrate the occlusion and cause the sharp cutting edge to cut the occlusion as the blade assembly is advanced into the occlusion, wherein the step of advancing the blade assembly comprises advancing the blade assembly with the sharp cutting edge starting within the elongate passageway to outside the elongate passageway to engage the occlusion.

2. The method of penetrating an intravascular occlusion according to claim 1 wherein the stabilizing assembly comprises an elongate probe with a penetrating tip and the step of stabilizing the sleeve assembly comprises advancing the elongate probe in the first lengthwise direction to cause the penetrating tip to penetrate the occlusion at the one of the spaced axial locations.

3. The method of penetrating an intravascular occlusion according to claim 2 wherein the stabilizing assembly comprises an inflatable bladder and the step of stabilizing the sleeve assembly comprises inflating the bladder to thereby change the stabilizing assembly from its first state into its second state.

4. The method of penetrating an intravascular occlusion according to claim 2 wherein the penetrating tip has a granular component thereon to facilitate penetration of the occlusion.

5. The method of penetrating an intravascular occlusion according to claim 2 further comprising the step of rotating at least one of the penetrating tip and blade assembly around an axis to penetrate the occlusion.

6. The method of penetrating an intravascular occlusion according to claim 1 wherein the blade assembly comprises a plurality of blades that taper to a tip and the step of advancing the blade assembly comprises advancing the blade assembly tip forward in the first lengthwise direction into the occlusion.

7. The method of penetrating an intravascular occlusion according to claim 1 further comprising the step of directing a guide wire into the vessel passage toward the occlusion and the step of directing the sleeve assembly into its operative position comprises guiding the sleeve assembly along the guide wire in the first lengthwise direction.

8. The method of penetrating an intravascular occlusion according to claim 1 further comprising the step of advancing a guide wire through the occlusion after the blade assembly has penetrated fully through the occlusion and thereafter removing the blade assembly from the passageway.

9. The method of penetrating an intravascular occlusion according to claim 1 wherein the sleeve assembly comprises a tapered annular surface that reduces in diameter in the first lengthwise direction and the step of advancing the blade assembly comprises advancing the blade assembly guidingly against the tapered annular surface.

10. The method of penetrating an intravascular occlusion according to claim 1 wherein the blade assembly has an axis and the blade assembly comprises a plurality of blades spaced from each other around the blade assembly axis.

11. The method of penetrating an intravascular occlusion according to claim 1 wherein the step of advancing the blade assembly comprises causing the blade assembly to produce an enlarged bore diameter through the occlusion.

12. A method of penetrating an intravascular occlusion, the method comprising the steps of:
obtaining an apparatus comprising a sleeve assembly defining an elongate passageway with a lengthwise axis, a stabilizing assembly, and a blade assembly comprising a plurality of blades each with a body having a generally flat shape that projects radially outwardly from the lengthwise axis;
directing the sleeve assembly into an operative position within a vessel passage wherein an outlet from the elongate passageway is adjacent an occlusion within the vessel passage;
through the stabilizing assembly, stabilizing the sleeve assembly in the operative position; and
with the sleeve assembly stabilized in its operative position advancing the blade assembly in a first lengthwise direction relative to the sleeve assembly to penetrate the occlusion,
wherein the stabilizing assembly comprises an elongate probe with a penetrating tip and the step of stabilizing the sleeve assembly comprises advancing the elongate probe in the first lengthwise direction to cause the penetrating tip to penetrate the occlusion,
wherein the step of advancing the blade assembly comprises guiding the blade assembly against and relative to the elongate probe.

13. The method of penetrating an intravascular occlusion according to claim 12 wherein the blade assembly comprises a flat cutting blade.

14. The method of penetrating an intravascular occlusion according to claim 12 wherein the planes of the bodies align with the lengthwise axis.

15. The method of penetrating an intravascular occlusion according to claim 12 wherein the bodies of the blades each has a fin shape that projects radially with respect to the lengthwise axis.

16. A method of penetrating an intravascular occlusion, the method comprising the steps of:
obtaining an apparatus comprising a sleeve assembly defining an elongate passageway with a lengthwise axis, a stabilizing assembly, and a blade assembly;
directing a guide wire into a vessel passage toward the occlusion;
directing the sleeve assembly into an operative position within the vessel passage wherein an outlet from the elongate passageway is adjacent an occlusion within the vessel passage;
through the stabilizing assembly, stabilizing the sleeve assembly in the operative position at spaced axial locations wherein at one of the spaced axial locations a part of the stabilizing assembly penetrates the occlusion;
with the sleeve assembly stabilized in its operative position advancing the blade assembly in a first lengthwise direction relative to the sleeve assembly to penetrate the occlusion,
wherein the step of directing the sleeve assembly into its operative position comprises guiding the sleeve assembly along the guide wire in the first lengthwise direction,
wherein the stabilizing assembly comprises an elongate probe with a penetrating tip and the step of stabilizing the sleeve assembly comprises advancing the elongate probe in the first lengthwise direction to cause the penetrating tip to penetrate the occlusion; and
removing the guide wire from the passageway before directing the elongate probe into the passageway,
wherein the blade assembly is advanced guidingly along the elongate probe to penetrate the occlusion.

17. A method of penetrating an intravascular occlusion, the method comprising the steps of:
obtaining an apparatus comprising a sleeve assembly defining an elongate passageway with a lengthwise axis, a stabilizing assembly, and a blade assembly with a sharp cutting edge;

directing the sleeve assembly into an operative position within a vessel passage wherein an outlet from the elongate passageway is adjacent an occlusion within the vessel passage;

through the stabilizing assembly, stabilizing the sleeve assembly in the operative position; and with the sleeve assembly stabilized in its operative position advancing the sharp cutting edge in a first lengthwise direction relative to the sleeve assembly from within the elongate passageway to outside the elongate passageway to penetrate the occlusion and cause the sharp cutting edge to cut the occlusion as the blade assembly is advanced into the occlusion, wherein the stabilizing assembly is changeable between first and second states, the stabilizing assembly configured to be extended radially outwardly from the sleeve assembly as the stabilizing assembly is changed from its first state into its second state to thereby limit radial skewing of the sleeve assembly within the vessel passage, wherein the stabilizing assembly comprises an inflatable bladder and the step of stabilizing the sleeve assembly comprises inflating the bladder to thereby change the stabilizing assembly from its first state into its second state, wherein the stabilizing assembly further comprises a guide wire and the step of stabilizing the sleeve assembly comprises directing the guide wire in the first longitudinal direction so that the guide wire is stabilized by the occlusion after which the bladder is changed from its first state into its second state while maintaining the part of the guide wire stabilized by the occlusion.

18. A method of penetrating an intravascular occlusion, the method comprising the steps of:

obtaining an apparatus comprising a sleeve assembly defining an elongate passageway with a lengthwise axis, a stabilizing assembly, and a blade assembly;

directing the sleeve assembly into an operative position within a vessel passage wherein an outlet from the elongate passageway is adjacent an occlusion within the vessel passage;

through the stabilizing assembly, stabilizing the sleeve assembly in the operative position;

with the sleeve assembly stabilized in its operative position advancing the blade assembly in a first lengthwise direction relative to the sleeve assembly to penetrate the occlusion, wherein the stabilizing assembly is changeable between first and second states, the stabilizing assembly configured to be extended radially outwardly from the sleeve assembly as the stabilizing assembly is changed from its first state into its second state to thereby limit radial skewing of the sleeve assembly within the vessel passage, wherein the stabilizing assembly comprises an inflatable bladder and the step of stabilizing the sleeve assembly comprises inflating the bladder to thereby change the stabilizing assembly from its first state into its second state, wherein the stabilizing assembly further comprises a guide wire and the step of stabilizing the sleeve assembly comprises directing the guide wire in the first longitudinal direction into the occlusion after which the bladder is changed from its first state into its second state;

removing the guide wire;

directing an elongate probe with a penetrating tip into the passageway in the first longitudinal direction so that the penetrating tip penetrates the occlusion; and after directing the elongate probe into the passageway, advancing the blade assembly in the first longitudinal direction against and relative to the elongate probe and into the occlusion.

19. The method of penetrating an intravascular occlusion according to claim 18 further comprising the step of removing the elongate probe and blade assembly after the occlusion has been fully penetrated and thereafter directing a guide wire into the passageway in the first longitudinal direction and to and through the occlusion with the elongate probe removed.

20. The method of penetrating an intravascular occlusion according to claim 19 further comprising the step of guiding a device through the passageway and over and against the guide wire through the occlusion to allow performance of a procedure by the device within the vessel passage past the occlusion.

21. A method of penetrating an intravascular occlusion the method comprising the steps of:

obtaining an apparatus comprising a sleeve assembly defining an elongate passageway with a lengthwise axis, a stabilizing assembly, and a blade assembly;

directing the sleeve assembly into an operative position within a vessel passage wherein an outlet from the elongate passageway is adjacent an occlusion within the vessel passage;

through the stabilizing assembly, stabilizing the sleeve assembly in the operative position at spaced axial locations wherein at one of the spaced axial locations a part of the stabilizing assembly penetrates the occlusion; and with the sleeve assembly stabilized in its operative position advancing the blade assembly in a first lengthwise direction relative to the sleeve assembly to penetrate the occlusion, wherein the blade assembly comprises a plurality of blades that taper to a tip and the step of advancing the blade assembly comprises advancing the blade assembly tip forward in the first lengthwise direction into the occlusion, wherein the step of advancing the blade assembly comprises advancing the blade assembly in a curved path within the vessel passage and thereby causing the blades to bend to conform to the curved path.

22. A method of penetrating an intravascular occlusion, the method comprising the steps of:

obtaining an apparatus comprising a sleeve assembly defining an elongate passageway with a lengthwise axis, a stabilizing assembly, and a blade assembly;

directing the sleeve assembly into an operative position within a vessel passage wherein an outlet from the elongate passageway is adjacent an occlusion within the vessel passage;

through the stabilizing assembly, stabilizing the sleeve assembly in the operative position at spaced axial locations wherein at one of the spaced axial locations a part of the stabilizing assembly penetrates the occlusion, wherein the stabilizing assembly is changeable between first and second states, a part of the stabilizing assembly configured to be extended radially outwardly from the sleeve assembly as the stabilizing assembly is changed from the first state into the second state, wherein the step of stabilizing the sleeve assembly comprises changing the stabilizing assembly from the first state into the second state while maintaining the part of the stabilizing assembly penetrating the occlusion; and with the sleeve assembly stabilized in its operative position advancing the blade assembly in a first lengthwise direction relative to the sleeve assembly to penetrate the occlusion, wherein the vessel passage has a length and the blade assembly comprises a flat blade with a plane that aligns with the length of the vessel passage.

23. A method of penetrating an intravascular occlusion, the method comprising the steps of:

obtaining an apparatus comprising a sleeve assembly defining an elongate passageway with a lengthwise axis, a stabilizing assembly, and a blade assembly;

directing the sleeve assembly into an operative position within a vessel passage wherein an outlet from the elongate passageway is adjacent an occlusion within the vessel passage;

through the stabilizing assembly, stabilizing the sleeve assembly in the operative position at spaced axial locations wherein at one of the spaced axial locations a part of the stabilizing assembly penetrates the occlusion, wherein the stabilizing assembly is changeable between first and second states, a part of the stabilizing assembly configured to be extended radially outwardly from the sleeve assembly as the stabilizing assembly is changed from the first state into the second state, wherein the step of stabilizing the sleeve assembly comprises changing the stabilizing assembly from the first state into the second state while maintaining the part of the stabilizing assembly penetrating the occlusion; and with the sleeve assembly stabilized in its operative position advancing the blade assembly in a first lengthwise direction relative to the sleeve assembly to penetrate the occlusion, wherein the blade assembly comprises a plurality of blades that taper to a tip and the step of advancing the blade assembly comprises advancing the blade assembly tip forward in the first lengthwise direction into the occlusion, wherein each of the blades tapers to a tip at an end of the blade assembly.

24. A method of penetrating an intravascular occlusion, the method comprising the steps of:

obtaining an apparatus comprising a sleeve assembly defining an elongate passageway with a lengthwise axis, a stabilizing assembly, and a blade assembly with a sharp cutting edge;

directing the sleeve assembly into an operative position within a vessel passage wherein an outlet from the elongate passageway is adjacent an occlusion within the vessel passage;

through the stabilizing assembly, stabilizing the sleeve assembly in the operative position at spaced axial locations wherein at one of the spaced axial locations a part of the stabilizing assembly is stabilized by the occlusion; and with the sleeve assembly stabilized in its operative position advancing the sharp cutting edge in a first lengthwise direction relative to the sleeve assembly from within the elongate passageway to outside the elongate passageway to penetrate the occlusion and cause the sharp cutting edge to cut the occlusion as the blade assembly is advanced into the occlusion, wherein the blade assembly comprises a flat blade.

25. The method of penetrating an intravascular occlusion according to claim 24 wherein the blade assembly has an axis and comprises a plurality of blades spaced from each other around the blade assembly axis.

26. A method of penetrating an intravascular occlusion, the method comprising the steps of:

obtaining an apparatus comprising a sleeve assembly defining an elongate passageway with a lengthwise axis, a stabilizing assembly, and a blade assembly with a sharp cutting edge;

directing the sleeve assembly into an operative position within a vessel passage wherein an outlet from the elongate passageway is adjacent an occlusion within the vessel passage;

through the stabilizing assembly, stabilizing the sleeve assembly in the operative position at spaced axial locations wherein at one of the spaced axial locations a part of the stabilizing assembly is pressed into material defining the occlusion so that the occlusion material closely surrounds and thereby stabilizes the part of the stabilizing assembly, wherein the stabilizing assembly is changeable between first and second states, another part of the stabilizing assembly configured to be extended radially outwardly from the sleeve assembly as the stabilizing assembly is changed from the first state into the second state, wherein the step of stabilizing the sleeve assembly comprises changing the stabilizing assembly from the first state into the second state while maintaining the part of the stabilizing assembly pressed into the material defining the occlusion; and with the sleeve assembly stabilized in its operative position advancing the blade assembly in a first lengthwise direction relative to the sleeve assembly to penetrate the occlusion and cause the sharp cutting edge to cut the occlusion as the blade assembly is advanced into the occlusion, wherein the step of advancing the blade assembly comprises advancing the blade assembly with the sharp cutting edge starting within the elongate passageway to outside of the elongate passageway to engage the occlusion.

* * * * *